(12) United States Patent
Khalili et al.

(10) Patent No.: US 7,455,695 B2
(45) Date of Patent: Nov. 25, 2008

(54) MODULAR PROSTHESIS AND LOCKING NUT THEREFOR

(75) Inventors: Bruce Khalili, Briarclif Manor, NY (US); Nadine Roth, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 450 days.

(21) Appl. No.: 10/878,291

(22) Filed: Jun. 28, 2004

(65) Prior Publication Data

US 2005/0288794 A1   Dec. 29, 2005

(51) Int. Cl.
*A61F 2/32* (2006.01)
*A61F 2/36* (2006.01)

(52) U.S. Cl. .............. 623/22.42; 623/23.11; 623/23.18; 623/23.35; 623/22.41

(58) Field of Classification Search .............. 623/22.42, 623/23.11–23.47, 22.41
See application file for complete search history.

(56) References Cited

U.S. PATENT DOCUMENTS

| | | | |
|---|---|---|---|
| 2,391,712 A | 12/1945 | King et al. | |
| 3,067,740 A | 12/1962 | Haboush | |
| 3,265,109 A | 8/1966 | Hanfland | |
| 4,995,883 A | 2/1991 | Demane et al. | |
| 5,002,578 A | 3/1991 | Luman | |
| 5,080,685 A * | 1/1992 | Bolesky et al. | 623/22.42 |
| 5,108,452 A | 4/1992 | DeMane et al. | |
| 5,147,363 A * | 9/1992 | Harle | 606/73 |
| 5,181,928 A | 1/1993 | Bolesky et al. | |
| 5,330,535 A | 7/1994 | Moser et al. | |
| 5,405,396 A | 4/1995 | Heldreth et al. | |
| 5,456,719 A | 10/1995 | Keller | |
| 5,507,830 A | 4/1996 | DeMane et al. | |
| 5,653,765 A | 8/1997 | McTighe et al. | |

(Continued)

FOREIGN PATENT DOCUMENTS

EP    0 567 349    10/1993

(Continued)

*Primary Examiner*—Bruce E. Snow
(74) *Attorney, Agent, or Firm*—Maginot, Moore & Beck

(57) ABSTRACT

A modular prosthesis is provided having a first and second prosthesis component and a locking nut. The first prosthesis component is configured to include a mating surface and a threaded shaft extending from the mating surface. The locking nut is formed to include a distal end having a shaped surface. The second prosthesis component is configured to include a mating surface, a nut-receiving cavity and a bore. The mating surface of the second prosthesis component is configured to mate with the mating surface of the first prosthesis component. The nut-receiving cavity is configured to receive the locking nut therein and to have a shaped bottom wall configured to engage the shaped surface of the locking nut. The bore communicates with the nut-receiving cavity through the shaped bottom wall and the mating surface and is sized to receive the threaded shaft therethrough. The threaded shaft, locking nut, bore and cavity are configured so that when the threaded shaft of the first prosthesis extends through the bore and the locking nut is received in the nut-receiving cavity and tightened onto the threaded shaft, the distal end of the locking nut is urged into engagement in multiple locations with the bottom wall of the cavity and the mating surfaces of the first and second components are urged into engagement.

3 Claims, 5 Drawing Sheets

U.S. PATENT DOCUMENTS

| | | | |
|---|---|---|---|
| 5,662,443 A | 9/1997 | Dziaba | |
| 5,725,592 A | 3/1998 | White et al. | |
| 5,876,459 A | 3/1999 | Powell | |
| 5,906,644 A | 5/1999 | Powell | |
| 6,045,310 A * | 4/2000 | Miller et al. | 411/383 |
| 6,048,365 A | 4/2000 | Burrows et al. | |
| 6,067,701 A | 5/2000 | Vandewalle | |
| 6,090,146 A | 7/2000 | Rozow, III et al. | |
| 6,136,035 A | 10/2000 | Lob et al. | |
| 6,264,699 B1 | 7/2001 | Noiles et al. | |
| 6,319,286 B1 | 11/2001 | Fernandez et al. | |
| 6,355,068 B1 | 3/2002 | Doubler et al. | |
| 6,355,069 B1 | 3/2002 | DeCarlo, Jr. et al. | |
| 6,428,578 B2 | 8/2002 | White | |
| 6,440,171 B1 | 8/2002 | Doubler et al. | |
| 6,905,515 B1 * | 6/2005 | Gilbertson | 623/22.4 |
| 2002/0038148 A1 | 3/2002 | Fernandez et al. | |
| 2002/0040244 A1 | 4/2002 | Despres, III et al. | |
| 2002/0042655 A1 | 4/2002 | Hayes, Jr. et al. | |
| 2002/0120343 A1 | 8/2002 | Doubler et al. | |
| 2003/0014119 A1 * | 1/2003 | Capon et al. | 623/19.11 |
| 2003/0074078 A1 | 4/2003 | Doubler et al. | |

FOREIGN PATENT DOCUMENTS

| | | |
|---|---|---|
| EP | 0 382 429 | 12/1994 |
| EP | 0 832 620 | 4/1998 |
| EP | 1 004 283 | 5/2000 |
| WO | WO 9601086 | 1/1996 |
| WO | WO 9808467 | 3/1998 |
| WO | WO 9808468 | 5/1998 |
| WO | WO 0167997 | 9/2001 |
| WO | WO 0170140 | 9/2001 |
| WO | WO 03/094803 | 11/2003 |

* cited by examiner

MODULAR PROSTHESIS AND LOCKING NUT THEREFOR

BACKGROUND AND SUMMARY

This invention relates generally to modular prosthesis and more particularly to modular prosthesis having a plurality of distal components adapted to be mounted to a proximal component with a locking nut.

In many total joint devices, longer stems are employed in either more difficult cases or cases with abnormal anatomy. A distally modular stem is desirable since it allows positioning of the distal stem consistent with the patient's anatomy while independently positioning the proximal body in order to optimize the biomechanics. Firm locking of the proximal body and distal stem is critical to the success of such a modular stem. Two critical concerns to clinicians are that the components could disassociate or fracture in vivo.

Many modular prosthetic systems are available that couple a distal stem to a proximal component. Often this coupling is accomplished using a Morse-type taper joint with the frusto-conical male portion of the joint being formed on one component while the female frusto-conical cavity is formed on the other component. In several such devices a fastener is utilized to aid the taper joint in remaining associated in vivo.

U.S. Pat. No. 6,090,146 discloses a male/female connecting joint between an implant body component and a stem component with a fastener that engages the implant components and draws them together. Thus, the device disclosed therein attempts to address concerns about disassociation of the implant components in vivo. However, the device disclosed therein does not fully address the risk of fracture in vivo.

Often the fasteners utilized to couple components of modular prosthesis together are configured to non-uniformly transfer stresses experienced by the fastener to the adjacent prosthesis components. Typically such fasteners are inserted into a nut receiving-cavity that has a flat bottom surface. When a standard locking nut is screwed onto a threaded shaft disposed in such a cavity, the nut (when the device is under stress) may contact the bottom surface of the cavity at a single point resulting in the stresses being non-uniformly transferred. This non-uniform distribution of stresses may induce the prosthesis components to fracture under stress. Thus, a fastener for securing the components of a modular prosthesis together which addresses both the concerns of disassociation and fracture of the components in vivo would be appreciated.

The disclosed modular prosthesis components and locking nut therefor address the concerns regarding disassociation and fracture of prosthesis components in vivo. The disclosed modular prosthesis components utilize a locking nut received in a cavity in one component of the prosthesis which is secured to the threaded shaft of the other component of the prosthesis to inhibit disassociation of the prosthesis components. The locking nut and cavity are formed to engage each other in multiple locations when the locking nut is tightened to address concerns regarding fracture of the prosthesis components.

According to one aspect of the invention, a modular prosthesis is provided that includes a first prosthesis component, a second prosthesis component and a locking nut. The first prosthesis component is configured to include a first half of a male/female connecting joint and a threaded shaft configured to receive the locking nut thereon. The second prosthesis component is formed to include a second half of a male/female connecting joint, a cavity configured to receive the locking nut therein and a bore communicating with the cavity and the second half of the male/female connecting joint and sized to receive the threaded shaft therethrough. The nut-receiving cavity is formed to include a shaped bottom surface through which the bore extends. The locking nut is formed to include a distal end having a shape configured to cooperate with the shaped bottom surface of the nut receiving cavity to create multiple locations of engagement. The threaded shaft, locking nut, bore and cavity are configured so that when the locking nut is tightened onto the threaded shaft the distal end of the locking nut is urged into engagement in multiple locations with the bottom surface of the cavity.

According to another aspect of the invention, a modular prosthesis is provided that includes a first prosthesis component, a second prosthesis component and a locking nut. The first prosthesis component is configured to include a mating surface and a threaded shaft extending from the mating surface and configured to receive the locking nut thereon. The second prosthesis component is formed to include a mating surface, a cavity configured to receive the locking nut therein and a bore communicating with the cavity and the mating surface and sized to receive the threaded shaft therethrough. The nut receiving cavity is formed to include a shaped bottom surface through which the bore extends. The locking nut is formed to include a distal end having a shape configured to cooperate with the shaped bottom surface of the nut-receiving cavity to create multiple locations of engagement. The threaded shaft, locking nut, bore and cavity are configured so that when the threaded shaft of the first prosthesis extends through the bore and the locking nut is tightened onto the threaded shaft the distal end of the locking nut is urged into engagement in multiple locations with the bottom surface of the cavity and the mating surfaces of the first and second components are urged into engagement.

According to yet another aspect of the invention, a modular prosthesis includes a distal prosthesis component, a locking nut and a proximal prosthesis component. The distal prosthesis component is configured to include a male joint component, a threaded shaft, a stem and an axis. The male joint component and threaded shaft are formed concentrically about the axis. The threaded shaft extends proximally from the male joint component and the stem extends distally from the male joint component. The locking nut is configured to be received on the threaded shaft and formed to include a radiused distal end exhibiting a radius of curvature. The proximal prosthesis component comprises a body having a longitudinal axis. The body is configured to include a female joint component configured to mate with the male joint component, a nut-receiving cavity and a shaft-receiving bore formed concentrically about the longitudinal axis. The nut-receiving cavity is configured to receive the locking nut therein and includes a radiused bottom surface exhibiting a radius of curvature configured to cooperate with the radiused distal end of the locking nut to create multiple locations of engagement. The bore is sized to receive the threaded shaft therein and communicates with the nut-receiving cavity through the radiused bottom surface and the female joint component. The threaded shaft, locking nut, bore and cavity are configured so that when the locking nut is tightened onto the threaded shaft the radiused distal end of the locking nut is urged into engagement in multiple locations with the radiused bottom surface of the cavity. A plurality of such proximal prosthesis components having differently sized bodies but similarly sized female joint components may be provided. A plurality of such distal prosthesis components may be provided having differently sized stems but similarly sized male joint components. A plurality of such locking nuts may be provided having different lengths but similar diameters.

Additional features and advantages of the present invention will become apparent to those skilled in the art upon consideration of the following detailed description of preferred embodiments exemplifying the best mode of carrying out the invention as presently perceived.

BRIEF DESCRIPTION OF THE DRAWINGS

The illustrative devices will be described hereinafter with reference to the attached drawings which are given as non-limiting examples only, in which.

Corresponding reference characters indicate corresponding parts throughout the several views. Like reference characters tend to indicate like parts throughout the several views.

DETAILED DESCRIPTION

Figure 1:
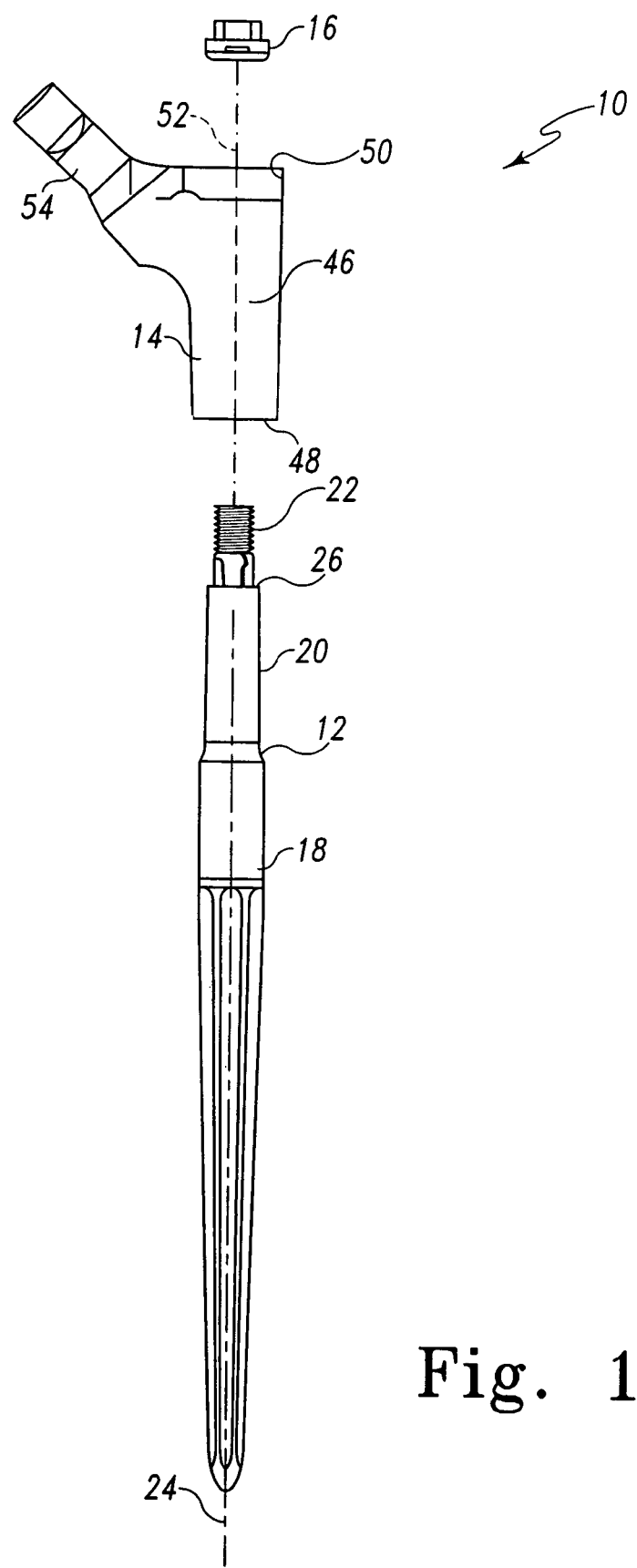
FIG. 1 is an exploded view of a modular prosthesis including a distal stem component having a threaded shaft extending therefrom, a proximal body component and a locking nut for securing the distal stem component to the proximal body component.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

As shown for example, in FIGS. 1-11, a modular prosthesis 10 includes a distal stem component 12, a proximal body component 14 and a locking nut 16. The illustrated modular prosthesis 10 includes components that can be mated to form a component of a hip prosthesis for attachment to the femur of a patient. While not illustrated, the modular prosthesis 10 may also include a plurality of differently sized heads each configured to couple to the proximal end of the proximal body component 14 and a plurality of hip socket or acetabular cup components configured to allow appropriately sized heads to articulate therein. While the invention is described with regard to a hip prosthesis, it is within the scope of the disclosure for the invention to be applied to other modular prosthesis, including, but not limited to knee, elbow and shoulder prosthesis.

Although the illustrations show only one of the distal stem component 12, those skilled in the art will recognize that modular prosthesis 10 are typically provided as part of a system that includes a plurality of differently sized distal stem components 12 all configured to mate with any of a plurality of differently sized proximal body components 14 so that the surgeon can create an appropriately configured prosthesis for the patient's anatomy.

The illustrated distal stem component 12 includes a stem 18, a male joint component 20, a threaded shaft 22 and a longitudinal axis 24. In the illustrated embodiment, the male joint component 20 is configured to serve as the male component of a Morse-type taper lock joint. Thus, male joint component 20 includes a circular proximal end wall 26, a circular distal end wall 28 (which in the illustrated embodiment merges with the stem portion 18) and a frusto-conical side wall 30 each formed concentrically about longitudinal axis 24. The frusto conical side wall 30 extends between and couples the edges of the proximal end wall 26 and the distal end wall 28. In one illustrative example of a male joint component for a Morse-type taper lock joint, the frusto-conical side wall 30 adjacent the proximal end wall 26 has a diameter 32 and adjacent the distal end wall 28 has a diameter 34. The male joint component 20 has a length 36. Thus, in the illustrated male joint component 20 the difference between diameter 32 and diameter 34 and the displacement between the locations where the male joint component 20 exhibits such diameters 32 and 34 is such that the male joint component 20 exhibits a taper angle of approximately two degrees. The male joint component is formed to include a full taper 72 that corresponds to a full taper 70 in the female joint component 56. The formation of Morse taper male components is known in the art and the description of the male joint component 20 contained herein should not be viewed as limiting.

Figures 2, 3, 4:
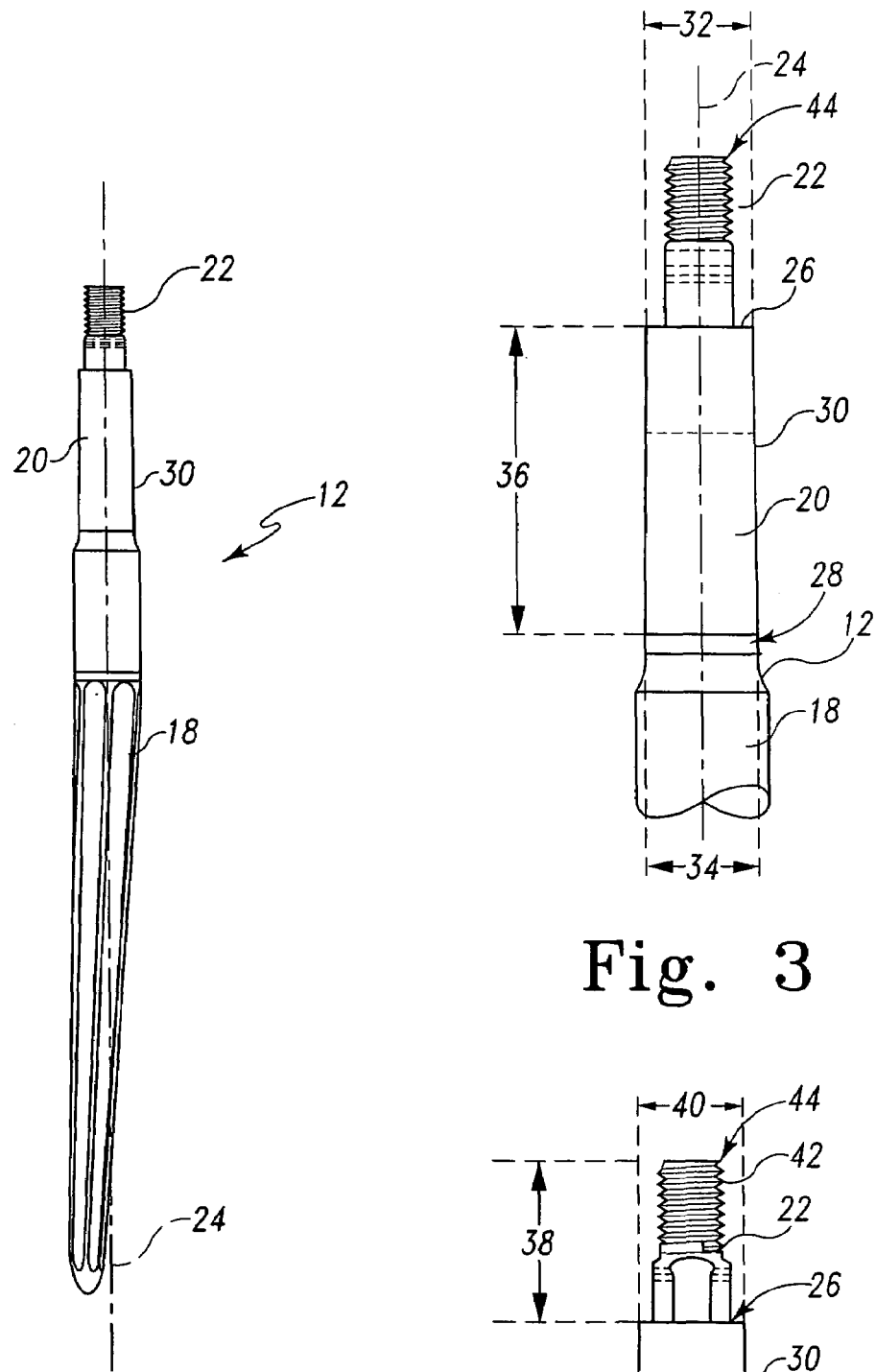
FIG. 2 is an elevation view of the distal stem component of FIG. 1 showing a stem component for insertion into the medullary canal of a patient mounted to a male joint component from which a threaded shaft extends.
FIG. 3 is an enlarged view of the male joint component and threaded shaft of the distal stem component of FIG. 2.
FIG. 4 is an enlarged view of the threaded shaft of the distal stem component of FIG. 1.

As shown, for example, in FIG. 2, the threaded shaft 22 extends from the proximal end wall 26 and the stem 18 extends from the distal end wall 28 of the male joint component 20. The threaded shaft 22 has a length 38, a diameter 40 and a thread 42 having a pitch and gage formed beginning at the proximal end 44 of the shaft 22 and extending toward the male joint component 20. The length 38 of the threaded shaft 22 is sufficient to extend through the bore 92 in the proximal body component 14 so that the proximal end 44 of the threaded shaft 22 is disposed in the nut-receiving cavity 78 when the male joint component 20 is seated within the female joint component 56. The diameter 40 of the threaded shaft 22 is slightly smaller than the diameter 96 of the bore 92 to facilitate passage of the threaded shaft 22 through the bore 92 as the body component 14 is coupled to the stem component 12. The external thread 42 on the threaded shaft 22 is of the same gauge and thread type as the internal thread 124 on the locking nut 16.

The stem 18 is configured to be received in the medullary canal. When multiple sizes of distal stem components 12 are provided in the modular prosthesis 10, typically the size of the stem 18 is different between different sized distal stem components 12. Those skilled in the art will recognize that the stem 18 is typically fluted and grit blasted or otherwise provided with an exterior finish to facilitate ingrowth and/or ongrowth of bone to provide stability to the prosthesis.

The proximal body component 14 is formed to include a body 46 having a distal surface 48, a proximal surface 50, an axis 52 and a head-mounting structure 54 extending at an angle from adjacent the proximal surface 50. As shown, for example, in FIGS. 6, 10 and 11, a female joint component 56 is formed in the body 46 extending through the distal surface 48. The female joint component 56 is configured to mate with the male joint component 20 to facilitate coupling the body component 14 to the stem component 12.

In the illustrated embodiment, female joint component 56 is configured to act as the female component of a Morse type taper lock. Thus, female joint component 56 is defined by a tapered side wall 58 extending between circular ends 60, 62 formed concentrically about the axis 52. The side wall 58 tapers inwardly as it extends into the body component 14 from a circular aperture 62 formed in the distal surface 48 concentrically about the axis 52 of the body component 14. In the illustrated embodiment, the tapered side wall 58 exhibits an approximately two degree taper to coincide with the approximately two degree taper of the male joint component 20 on the distal stem component 12. Illustratively, at a location adjacent the circular aperture 62 in the distal wall 48 at an appropriate location for mating with the male joint component 20, the tapered side wall 58 has a diameter 66 equal to diameter 34 of the male joint component 20. Illustratively, adjacent the circular end 60 the female joint component 56 has a diameter 64 that is equal to the diameter 32 of the male joint component 20. The female joint component 56 has an overall length 68 that is less than the length 36 of the male joint component 20. Within the female joint component 56 a full taper 70 is formed that conforms to the full taper 72 of the male joint component 20.

A nut-receiving cavity 78 is formed in the proximal body component 14. The nut-receiving cavity 78 is defined by a cylindrical side wall 80 and a curved end wall 82. Both the cylindrical side wall 80 and curved end wall 82 are formed symmetrically about the axis 52 of the proximal body component 14. A circular aperture 84 extends through the proximal wall 50 of the body component 14 to act as the opening to the nut-receiving cavity 78. The circular aperture 84 is formed concentrically about the axis 52 of the proximal body component 14.

The cylindrical side wall 80 of the nut-receiving cavity 78 has a diameter 86 which in the illustrated embodiment is 0.615 in. The diameter 86 of the cylindrical side wall 80 of the nut-receiving cavity 78 is selected to be slightly larger than the diameter 100 of the cylindrical side wall 102, 202 of each of the plurality of different length locking nuts 16, 116 to facilitate receipt of the appropriate locking nut 16, 116 in the nut-receiving cavity 78.

The curved end wall 82 of the nut-receiving cavity 78 has a radius of curvature 88 which in the illustrated embodiment is 0.375 in. The radius of curvature 88 of the curved end wall 82 of the nut-receiving cavity 78 is selected to cooperate with the radius of curvature 126 of the curved distal end wall 108 of the locking nut 16, 116 to facilitate engagement of the end wall 108 of the locking nut 16, 116 and the end wall 82 of the nut-receiving cavity 78 in multiple locations. In the illustrated embodiment, the radius of curvature 88 of the curved end wall 82 of the nut-receiving cavity 78 differs from the radiused curved distal end wall 108 of the locking nut 16, 116 to ensure that the curved end wall 82 of the nut-receiving cavity 78 engages the curved end wall 108 of the locking nut 16, 116 along a contiguous contact surface. In an alternative embodiment, the end wall 108 of the locking nut 16 and the end wall 82 of the nut-receiving cavity 78 are in contiguous contact across the entire surface 128 of the end wall 108 of the nut 16, 116.

Figure 6:
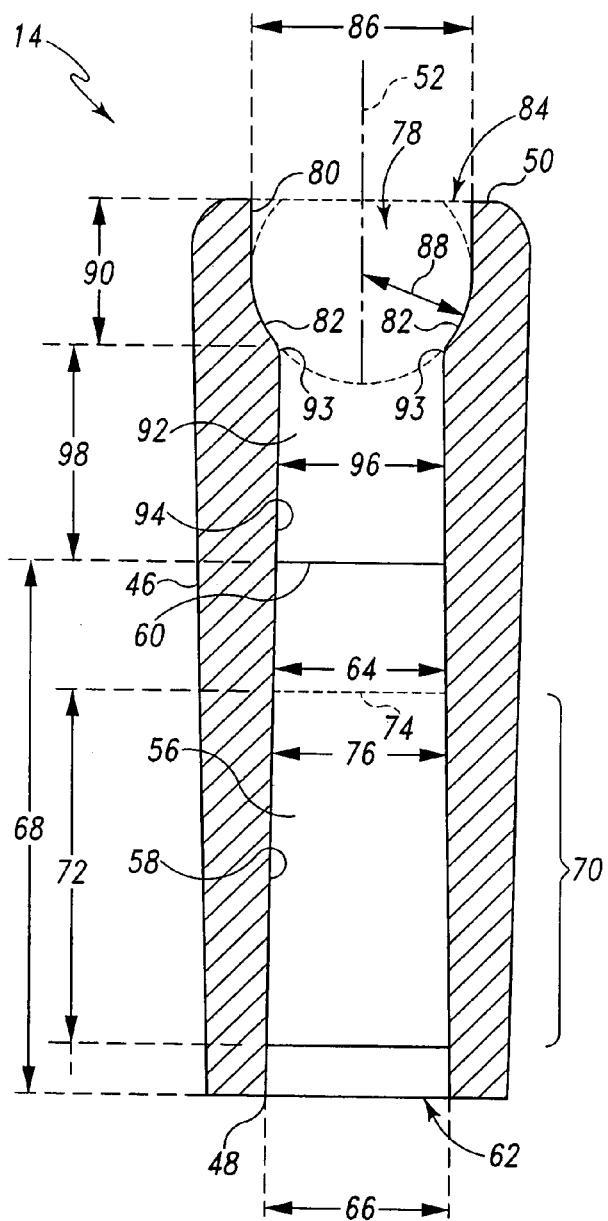
FIG. 6 is a sectional view taken along line 6-6 of the proximal body component of FIG. 5 showing a nut-receiving cavity having a radiused bottom wall, a bore and a female joint component formed in the proximal body component.
Figure 5:
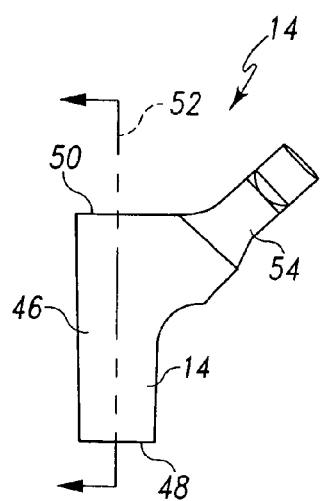
FIG. 5 is an elevation view of the proximal body component of the modular prosthesis of FIG. 1.
Figure 11:
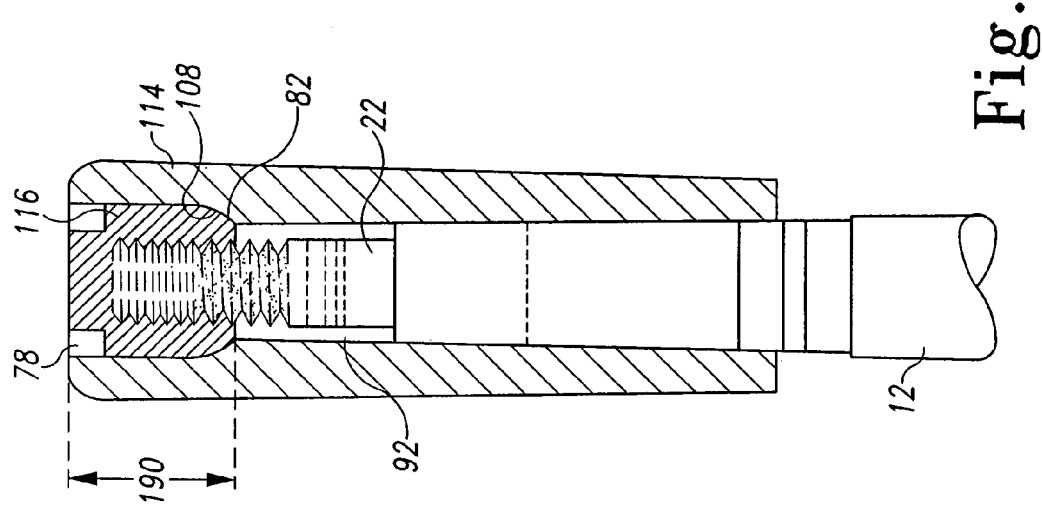
FIG. 11 is a view with parts of the proximal body component and locking nut broken away of an assembled modular prosthesis formed by mating a larger proximal body component formed to include a deeper nut-receiving cavity to the distal stem component and securing the components together with the locking nut of FIG. 9.
Figure 10:
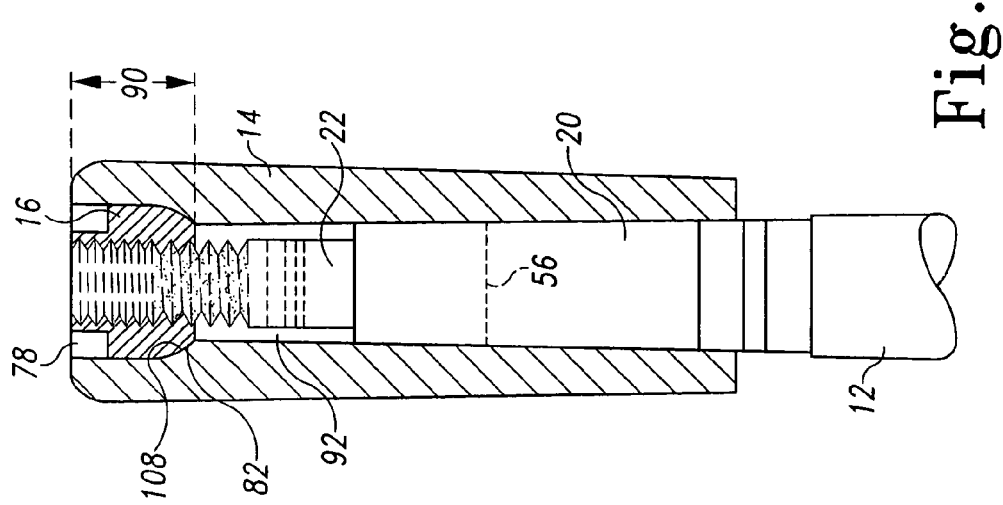
FIG. 10 is a view with parts of the proximal body component and locking nut broken away of the assembled modular prosthesis of FIG. 1 formed by mating the proximal body component to the distal stem component and securing the components together with the locking nut.

The nut-receiving cavity 78 has a depth 90, 190 which may vary, as shown, for example, in FIGS. 10 and 11, according to the size of the proximal body component 14, 114. In the illustrated proximal body component of FIGS. 6 and 10, the depth 90 of the nut-receiving cavity 78 is 0.381 in. The proximal body component 14 shown in FIGS. 6 and 10 is intended for use with a locking nut 16 having an overall length of 0.381 in. Since the nut-receiving cavity 78 of proximal body component 14 has a depth 90 substantially equal to the overall length 99 of the locking nut 16, when the end wall 108 of the nut 16 and the end wall 82 of the nut-receiving cavity 78 are urged into engagement with each other when the nut 16 is tightened onto the threaded shaft 22 to secure the proximal body component 14 and distal stem component 12 together, the top wall of the locking nut 16 is flush with the proximal surface 50 of the proximal body component 14, as shown, for example, in FIG. 10.

The proximal body component 14, 114 is formed to include a shaft-receiving bore 92 extending between the end wall 82 of the nut-receiving cavity 78 and the end wall 60 of the female joint component 86. The shaft-receiving bore 92 is defined by a cylindrical wall 94 formed concentrically about the axis 52 of the proximal body component 14, 114. In the illustrated embodiment, the shaft-receiving bore 92 has a diameter 96 which is slightly larger than the diameter 40 of the threaded shaft 22 to facilitate receipt of the threaded shaft 22 through the bore 92. The cylindrical wall 94 merges smoothly with the circular end 60 of the female joint component 56. The shaft-receiving bore 92 has a length 98 that is less than the length 38 of the threaded shaft 22 so that when the shaft 22 extends through the bore 92 and the male joint component 20 is properly seated in the female joint component 56, the proximal end 44 of the threaded shaft 22 extends into the nut-receiving cavity 78 sufficiently for the locking nut 16 to be threaded onto the shaft 22.

As shown, for example, in FIG. 6, the junction surface 93 between the curved end wall 82 of the nut-receiving cavity 78 and the cylindrical side wall 94 of the bore 92 is radiused. The radiused junction surface 93 prevents the distal end wall 108 of the locking nut 16, 116 from engaging the junction surface 93 which would result in concentration of stresses which the disclosed prosthesis is configured to avoid.

Figure 7:
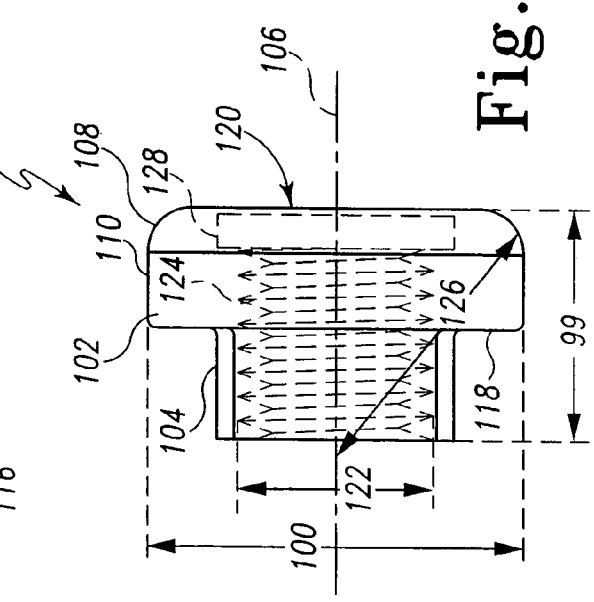
FIG. 7 is an elevation view of the locking nut of FIG. 1 showing the radiused bottom wall of the nut configured to engage the radiused bottom wall of the nut-receiving cavity of the proximal body component and showing, in phantom lines, the internal thread configured to cooperate with the thread of the threaded shaft of the distal stem component.
Figure 9:
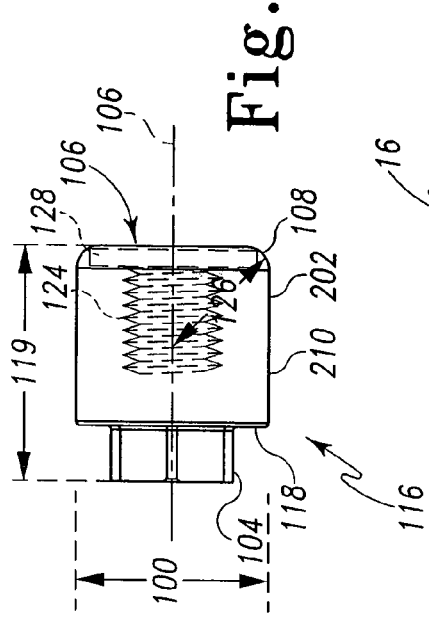
FIG. 9 is an elevation view of a locking nut configured to mate with a larger proximal body component formed to include a deeper locking nut-receiving cavity.
Figure 8:
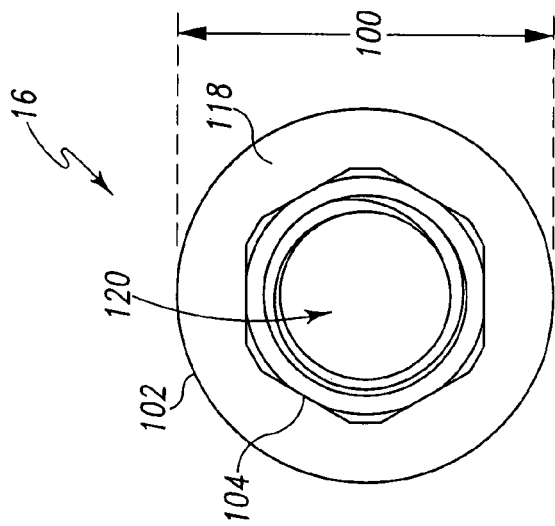
FIG. 8 is a plan view of the locking nut of FIG. 1 showing the hex-shaped head that facilitates using tools when tightening the locking nut onto a threaded shaft.

Referring to FIGS. 7, 8 and 9, two of a plurality of locking nuts 16, 116 are illustrated. In the illustrated embodiments, since each of the plurality of differently sized proximal body components 14, 114 includes a nut-receiving cavity 78 having the same diameter 86 but different depths 90, 190, each of the plurality of locking nuts 16, 116 have the same diameter 100 but differ in lengths 99, 199 so that each is appropriate for one of the plurality of proximal body components 14, 114. In the illustrated embodiment, the diameter 100 of locking nuts 16, 116 is approximately equal to but slightly less than the diameter 86 of the cylindrical wall 80 of the nut-receiving cavity 78 formed in the proximal body component 14, 114. Since in the illustrated embodiments, locking nuts 16, 116 differ only in length, similar reference numerals will be utilized to refer to similar components while identical reference numerals will be utilized to refer to identical components.

Each of the plurality of locking nuts 16, 116 includes a body 102, 202, a head 104 and a longitudinal axis 106. The body 102, 202 includes distal curved end wall 108, a cylindrical side wall 110, 210 and a top wall 118 formed concentrically about the longitudinal axis 106. The head 104 is coupled to the top wall 118 of the body 102, 202 and is configured to mate with a tool for driving the nut 16, 116 onto the threaded shaft 22. In the illustrated embodiments, the head 104 has a hexagonal configuration to facilitate use of a wrench or a socket when attaching the nut 16 to the threaded shaft 22. The head 104 is formed symmetrically about a plane extending through the longitudinal axis 106.

Curved end wall 108 is radiused 126 so as to cooperate with the radius of curvature 88 of the curved end wall 82 of the nut-receiving cavity 78 to form a surface contact between the two when they are brought into engagement. In the illustrated embodiment, the radius 126 of the curved end wall 108 is 0.080 In. In an alternative embodiment, curved end wall 108 may exhibit a radius of curvature identical to the radius of curvature 88 of the curved end wall 82 of the nut-receiving cavity 78 to facilitate contiguous contact between curved end wall 108 and curved end wall 82 along the entire surface of curved end wall 108.

An internally threaded bore 120 is formed concentrically about the longitudinal axis 106 and extends through the curved end wall 108. The bore 120 has a diameter 122 which in the illustrated embodiment is 0.317 in. The internal thread 124 of the bore 120 has a gage and pitch configured to match the gage and pitch of the threaded shaft 22.

As shown for example, in FIG. 7, locking nut 16 has a length 99 that in the illustrated embodiment is 0.381 in. Locking nut 16 is configured as the appropriate or associated nut for use with a proximal body component 14 having a locking nut-receiving cavity 78 having a depth 90 of 0.381 in. Thus, when locking nut 16 is positioned in the locking nut-receiving cavity 78 with the curved end wall 108 inserted first, the locking nut 16 can be screwed onto the distal end 44 of the threaded shaft 22 of a distal stem component 12 and tightened onto the shaft 22 to secure the distal stem component 12 to the proximal body component 14, as shown, for example, in FIG. 10. As previously mentioned, when locking nut 16 is inserted into the nut-receiving cavity 78 of proximal body component 14 and tightened onto the threaded shaft 22 to secure the proximal body component 14 and distal stem component 12 together, the top wall of the locking nut 16 is flush with the proximal surface 50 of the proximal body component 14, as shown, for example, in FIG. 10.

As the locking nut 16 is tightened onto the threaded shaft 22, the male joint component 20 is properly seated within the female joint component 56 and the curved end wall 108 of the nut 16 is brought into engagement with the curved end wall 82 of the nut-receiving cavity 78. Because the curved end wall 108 of the nut 16 exhibits a radius 126 and the curved end wall 82 of the nut-receiving cavity 78 exhibits a radius of curvature 88, the end walls 108 and 82 engage in multiple locations, preferably along a contact surface. The entire end wall 108 of the locking nut 16 may even contiguously engage the end wall 82 of the nut-receiving cavity 78 when the nut 16 is properly tightened on the threaded shaft 22, within the scope of the disclosure.

As shown for example, in FIG. 9, locking nut 116 has a length 199 that in the illustrated embodiment is 1.562 in. Locking nut 116 is configured as the appropriate or associated nut for use with a proximal body component 114 having a locking nut-receiving cavity 78 having a depth 190 of 1.562 in. Thus, when locking nut 116 is positioned in the locking nut-receiving cavity 78 with the curved end wall 108 inserted first, the locking nut 116 can be screwed onto the distal end 44 of the threaded shaft 22 of a distal stem component 12 and tightened onto the shaft 22 to secure the distal stem component 12 to the proximal body component 14, as shown, for example, in FIG. 11. Since the nut-receiving cavity 78 of proximal body component 114 has a depth 190 substantially equal to the overall length 199 of the locking nut 116, when the end wall 108 of the nut 116 and the end wall 82 of the nut-receiving cavity 78 are urged into engagement with each other as nut 116 is tightened onto the threaded shaft 22 to secure the proximal body component 114 and distal stem component 12 together, the top wall of the locking nut 116 is flush with the proximal surface 50 of the proximal body component 114, as shown, for example, in FIG. 11.

As the locking nut 116 is tightened onto the threaded shaft 22, the male joint component 20 is properly seated within the female joint component 56 and the curved end wall 108 of the nut 116 is brought into engagement with the curved end wall 82 of the nut-receiving cavity 78. Because the curved end wall 108 of the nut 116 exhibits a radius 126 and the curved end wall 82 of the nut-receiving cavity 78 exhibits a radius of curvature 88, the end walls 108 and 82 engage in multiple locations, preferably along a contact surface. The entire end wall 108 of the locking nut 116 may even contiguously engage the end wall 82 of the nut-receiving cavity 78 when the nut 116 is properly tightened on the threaded shaft 22, within the scope of the disclosure.

Since the end wall 108 of the nut 16, 116 engages the end wall 82 of the nut-receiving cavity 78 either contiguously or in multiple locations, stresses placed on the prosthesis 10 are transferred by the nut 16, 116 to the proximal body component 14, 114 more evenly than in prior art modular prosthesis utilizing nuts with flat end walls received in cavities with flat end walls. Such prior art prosthesis tend to have the nut contacting the end wall of the nut-receiving cavity at one or a few points rather than over contact surfaces. Tests on such prior art configurations and the prosthesis disclosed herein indicate the prosthesis configured as disclosed herein exhibit a reduction of stresses at the interface between the nut and the nut-receiving cavity as compared to such prior art configurations.

While the illustrated embodiment of the modular prosthesis is shown and described as having the male joint component 20 formed on the distal stem component 12 and the female joint component 56 formed in the proximal body component 14, it is within the scope of the disclosure for the male joint component 20 to be formed on the proximal body component and the female joint component 56 to be formed in the distal stem component. While the benefits of inserting the stem component into the medullary canal prior to mounting the body component thereto would not be easily recognized, it is nevertheless within the scope of the disclosure for the lock nut-receiving cavity 78 and bore 92 to be formed in the distal stem component and the threaded shaft 22 to extend from the proximal body component.

Those skilled in the art will recognize that other systems may be used for mounting the distal stem component 12 to the proximal body component 14 of the modular prosthesis 10. It is within the scope of the disclosure to utilize other taper lock systems or other mounting systems. It is also within the scope of the disclosure for no joint to be formed between the proximal body component 14 and the distal stem component 12. In such a case, each component will typically include a mating surface. In such a device, when the locking nut 16, 116 having the curved end wall 108 is received in the nut-receiving cavity 78 having a cooperating curved end wall 82 and tightened onto the threaded shaft 22, the mating surfaces of the stem component 12 and body component 14 are drawn into proximity of, or into engagement with, each other.

Although only two differently sized body components 14, 114 are illustrated and described, the disclosure envisions that a plurality of differently sized body components may be provided with each having similarly sized female sockets formed therein. Additionally, while only a single distal stem component 12 is illustrated and described, it is within the scope of the disclosure to provide a plurality of differently sized distal stem components each formed to include a male joint component configured to mount to each provided proximal body component. So that the threaded shaft of each distal stem component can be the same length, it is within the scope of the disclosure for the depth of the nut-receiving cavity to increase as the size of the proximal body component increases. Accordingly, a surgeon may form an appropriately sized and configured prosthesis by selecting from the provided plurality of distal stem components, proximal body components and locking nuts.

Those skilled in the art will recognize that the end wall 108 of the locking nut 16 could be formed to include a multiple radiused surface 128 configured to cooperate with a multiple radiused surface of the bottom wall 82 of the nut-receiving cavity 78 within the scope of the disclosure. In fact, it is within the scope of the disclosure for the end wall 108 of the locking nut 16 and the bottom wall 108 of the nut-receiving cavity 78 to be any non-planar shape that allows the nut to be tightened onto the threaded shaft to induce engagement of the end wall 108 and bottom wall 82 in multiple locations, over a surface area or contiguously along the surface of the end wall 108 of the nut 16. The engagement of the end wall 108 of the locking nut 16 and the bottom wall 82 of the nut-receiving cavity 78 aids in more evenly distributing stresses in the proximal body thereby reducing the likelihood of fracture of the prosthesis in vivo.

Although specific embodiments of the invention have been described herein, other embodiments may be perceived by those skilled in the art without departing from the scope of the invention as defined by the following claims.

What is claimed is:

1. A modular prosthesis kit comprising:
    a distal prosthesis component including a male joint component, a threaded shaft, a non-threaded stem for insertion within an intramedullary canal of a bone and an axis, wherein the male joint component and threaded shaft are formed concentrically about the axis and wherein the threaded shaft extends proximally from the male joint component and the stem extends distally from the male joint component;
    a locking nut including a distal end with a threaded bore for receiving the threaded shaft and a radiused, when viewed in cross-section, contact portion extending outwardly and proximally from the threaded bore to a side wall of the locking nut; and
    a proximal prosthesis component including a body, a female joint component within the body sized to receive the male joint component, a nut-receiving cavity with a radiused, when viewed in cross-section, bottom surface, a side wall substantially equal in height to the side wall of the locking nut, and a shaft-receiving bore opening to the nut-receiving cavity through the radiused bottom surface and to the female joint component and sized to receive the threaded shaft therein;
    a plurality of differently sized distal prosthesis components each including a male joint component, a threaded shaft, a non-threaded stem for insertion within an intramedullary canal of a bone and an axis, wherein the male joint component and threaded shaft are formed concentrically about the axis and wherein the threaded shaft extends proximally from the male joint component and the stem extends distally from the male joint component, wherein the stem of each of the plurality of distal prosthesis components is a different size than the stems of the other of the plurality of distal prosthesis components;
    a plurality of proximal prosthesis components each including a body, a female joint component within the body sized to receive the male joint component, a nut-receiving cavity with a radiused, when viewed in cross-section, bottom surface, a side wall substantially equal in height to the side wall of the locking nut, and a shaft-receiving bore opening to the nut-receiving cavity through the radiused bottom surface and to the female joint component and sized to receive the threaded shaft of at least one of the plurality of differently sized distal prosthesis components therein, wherein the body of each of the plurality of proximal prosthesis components is a different size than the body of the other of the plurality of proximal prosthesis components and the female joint components of all of the plurality of proximal prosthesis components are configured to receive the male joint component of each of the plurality of distal prosthesis components; and
    a plurality of locking nuts each having a diameter and a length and configured to be received on the threaded shaft of each of the plurality of distal prosthesis components, each of the plurality of locking nuts including a radiused, when viewed in cross-section, contact portion extending outwardly and proximally from the threaded bore to a side wall of the locking nut, wherein the diameter of each of the plurality of locking nuts is the same as the diameter of the other of the plurality of locking nuts and the side wall of each of the plurality of locking nuts is of a length different from the length of each of the other of the side walls; and wherein:
        the nut-receiving cavity of each of the plurality of proximal prosthesis components includes a diameter and a depth;
        the diameter of the nut-receiving cavity of each of the plurality of proximal prosthesis components is the same as the diameter of the nut-receiving cavity of the other of the plurality of proximal prosthesis components; and
        the depth of the nut-receiving cavity of each of the plurality of proximal prosthesis components is different from the depth of the nut-receiving cavity of each of the other of the plurality of proximal prosthesis components.

2. The modular prosthesis of claim 1 wherein each of the plurality of locking nuts is associated with a different one of the plurality of proximal prosthesis components.

3. The modular prosthesis of claim 2 wherein the length of the side wall of the associated one of the plurality of locking nuts is substantially equal to the depth of the nut-receiving cavity of its associated one of the plurality of proximal prosthesis components.

* * * * *